(12) United States Patent
Tanaka et al.

(10) Patent No.: US 11,836,923 B2
(45) Date of Patent: Dec. 5, 2023

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventors: Toru Tanaka, Chiba (JP); Ryo Ishikawa, Kanagawa (JP); Tatsuya Kimoto, Tochigi (JP); Hiroshi Moriya, Fukushima (JP)

(73) Assignee: Canon Kabushiki Kaisha, Tokyo (JP)

( * ) Notice: Subject to any disclaimer, the term of this patent is extended or adjusted under 35 U.S.C. 154(b) by 419 days.

(21) Appl. No.: 17/346,000

(22) Filed: Jun. 11, 2021

(65) Prior Publication Data

US 2021/0304409 A1    Sep. 30, 2021

Related U.S. Application Data

(63) Continuation of application No. PCT/JP2019/050752, filed on Dec. 25, 2019.

(30) Foreign Application Priority Data

Dec. 27, 2018 (JP) .................................. 2018-245138

(51) Int. Cl.
  *G06T 7/00* (2017.01)
  *G06T 7/73* (2017.01)
  *G06T 7/246* (2017.01)

(52) U.S. Cl.
  CPC ............ *G06T 7/0016* (2013.01); *G06T 7/248* (2017.01); *G06T 7/74* (2017.01); *G06T 2207/10016* (2013.01); *G06T 2207/10076* (2013.01); *G06T 2207/20221* (2013.01); *G06T 2207/30061* (2013.01)

(58) Field of Classification Search
  None
  See application file for complete search history.

(56) References Cited

U.S. PATENT DOCUMENTS

2018/0213107 A1* 7/2018 Momose .............. H04N 1/3876
2018/0213117 A1* 7/2018 Momose .............. H04N 1/3876

FOREIGN PATENT DOCUMENTS

| JP | 2004000411 A | 1/2004 |
| JP | 2011255055 A | 12/2011 |
| JP | 2016067832 A | 5/2016 |
| JP | 2017018317 A | 1/2017 |
| JP | 2017225724 A | 12/2017 |

* cited by examiner

*Primary Examiner* — Leon Flores
(74) *Attorney, Agent, or Firm* — Canon U.S.A., Inc. IP Division

(57) ABSTRACT

An image processing apparatus according to the present invention calculates, even in a case where a region of a part as an observation target included in an image capturing range is different between a plurality of medical images in different time phases, a degree of slippage of the region of the part as the observation target with high accuracy.

20 Claims, 8 Drawing Sheets

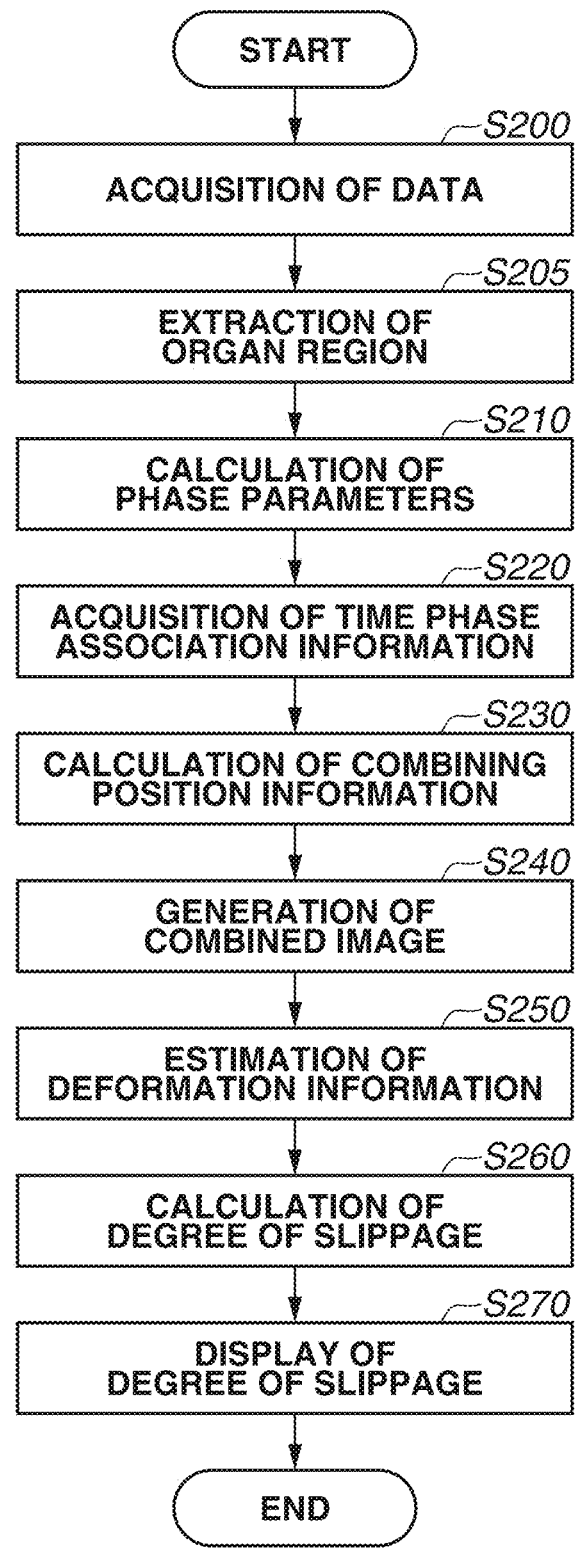

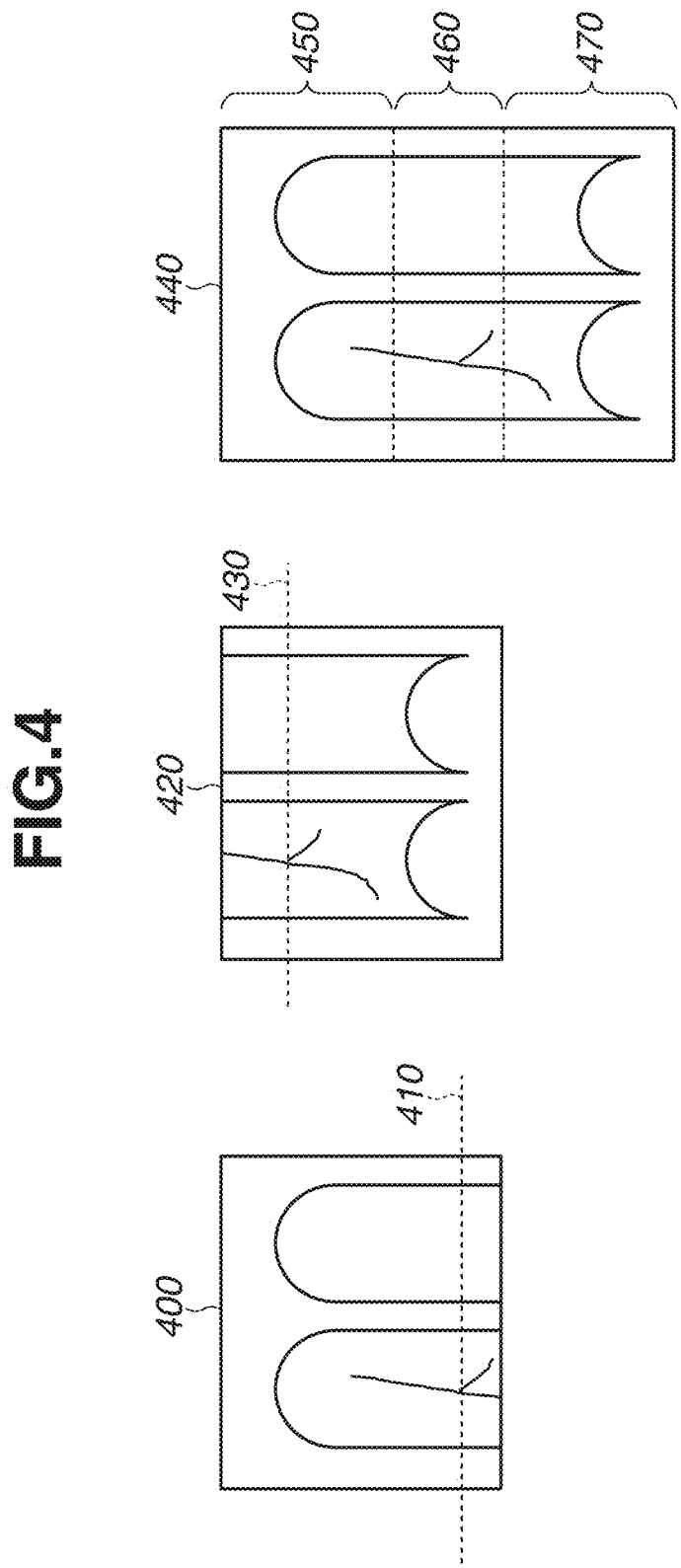

IMAGE PROCESSING APPARATUS, IMAGE PROCESSING METHOD, AND STORAGE MEDIUM

CROSS-REFERENCE TO RELATED APPLICATIONS

This application is a Continuation of International Patent Application No. PCT/JP2019/050752, filed Dec. 25, 2019, which claims the benefit of Japanese Patent Application No. 2018-245138, filed Dec. 27, 2018, both of which are hereby incorporated by reference herein in their entirety.

BACKGROUND OF THE INVENTION

Field of the Invention

The present invention relates to an image processing apparatus, an image processing method, and a storage medium.

Background Art

In the medical field, a doctor makes a diagnosis using medical images obtained by capturing a part as an observation target of a subject using various modalities. Particularly, in a case where a part in which the presence or absence of a disease appears in a motion of an organ, such as lungs and a heart, is observed, a plurality of medical images in different time phases can be used.

As a technique regarding a diagnosis using a plurality of medical images in different time phases, a technique for calculating a degree of slippage between two images obtained by capturing a region of a chest of the same patient in two time phases different in inspiratory volumes is known (PTL 1).

CITATION LIST

Patent Literature

PTL 1: Japanese Patent Laid-Open No. 2016-67832

PTL 1, however, has the issue that, in a case where a region of a part as an observation target included in an image capturing range is different between a plurality of medical images in different time phases since the part as the observation target moves, it is difficult to calculate a degree of slippage of the region of the part as the observation target.

SUMMARY OF THE INVENTION

The present invention is directed to providing an image processing apparatus capable of, even in a case where a region of a part as an observation target included in an image capturing range is different between a plurality of medical images in different time phases, calculating a degree of slippage of the region of the part as the observation target with high accuracy.

The present invention is not only directed to the above, but can also be directed to obtaining an operation and an effect that result from the configurations illustrated in the description of the embodiments below and cannot be obtained by a conventional technique.

According to an aspect of the present invention, an image processing apparatus includes a moving image acquisition unit configured to acquire a first moving image and a second moving image that have been obtained by capturing a target object from positions different from each other using an imaging apparatus, a generation unit configured to generate a first combined image by combining a first reference image obtained from the first moving image and a second reference image obtained from the second moving image, and generate a second combined image by combining a first comparison image obtained from the first moving image and a second comparison image obtained from the second moving image, and a degree-of-slippage calculation unit configured to calculate a degree of slippage of the target object, based on deformation information estimated from the first combined image and the second combined image.

Further features of the present invention will become apparent from the following description of exemplary embodiments with reference to the attached drawings.

BRIEF DESCRIPTION OF THE DRAWINGS

FIG. 2 is a flowchart illustrating an example of an entire processing procedure according to the first exemplary embodiment.

FIG. 4 is a diagram illustrating an example of a combining position according to the first exemplary embodiment.

DESCRIPTION OF THE EMBODIMENTS

Figure 1:
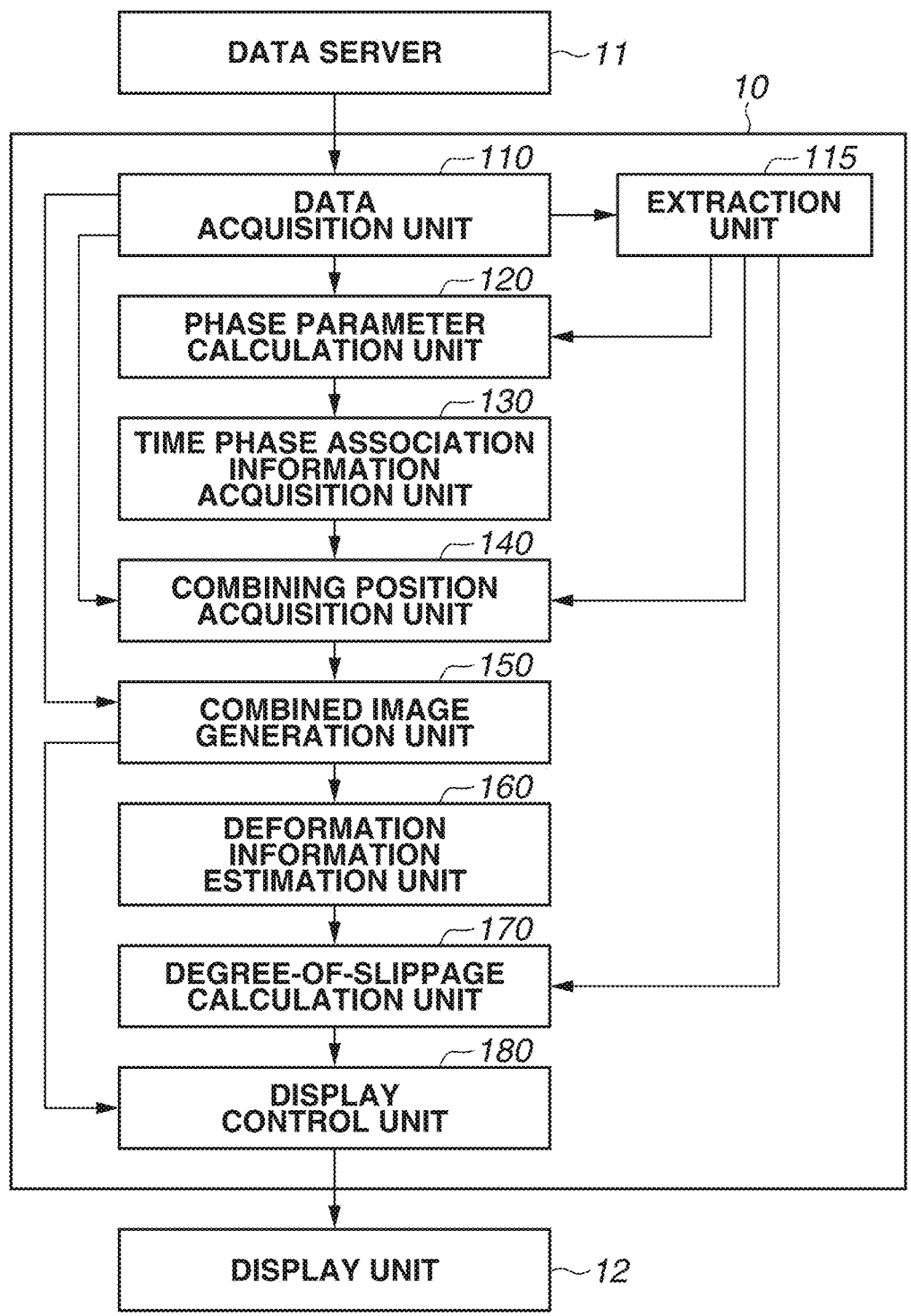
FIG. 1 is a diagram illustrating an example of a device configuration of an image processing apparatus according to a first exemplary embodiment.

With reference to the attached drawings, desirable exemplary embodiments of an image processing apparatus according to the present invention will be described in detail below. The components described in these exemplary embodiments, however, are merely illustrative. The technical scope of the image processing apparatus according to the present invention is determined by the appended claims, and is not limited by the following individual exemplary embodiments. The present invention is not limited to the following exemplary embodiments. Various modifications (including the organic combinations of the exemplary embodiments) can be made based on the spirit of the present invention, and are not excluded from the scope of the present invention. That is, all the configurations obtained by combining the following exemplary embodiments and their variations are also included in the exemplary embodiments of the present invention.

First Exemplary Embodiment

An image processing apparatus according to the present exemplary embodiment is an apparatus for calculating a degree of slippage near a contour of an entire region of an organ as an observation target using three-dimensional moving images (a first moving image and a second moving image) that have been captured the region of the organ multiple times in a divided manner while the observation target makes a periodic motion. The "degree of slippage" refers to movement information indicating to what degree a certain region in an image slips relative to a peripheral part. That is, the "degree of slippage" is the amount of movement of a target relative to a periphery of the target. For example, lungs move in such a manner that a surface (also termed a visceral pleura) of the lungs slips over a periphery (also termed a parietal pleura) of the lungs by a respiratory movement. In this case, the image processing apparatus according to the present exemplary embodiment displays a surface position of the lungs and a degree of slippage at the surface position in association with each other. In such display, if an adhesion occurs in a portion (also termed the pleural space) between the surface of the lungs and the periphery of the lungs, the degree of slippage is displayed smaller at the surface position where the adhesion is present than in a portion where an adhesion does not occur.

The image processing apparatus according to the present exemplary embodiment acquires a first moving image and a second moving image obtained by capturing an observation target (a target object) from positions different from each other using an imaging apparatus. Specifically, the image processing apparatus acquires the first and second moving images obtained by capturing the region of the observation target in a divided manner so that at least a part of the observation target is duplicate in each images. Then, the image processing apparatus analyzes the first moving image, to acquire a first phase parameter indicating phase information regarding the motion of the organ in time phase images in the first moving image (still images at clock times (in time phases) included in the first moving image). Similarly, the image processing apparatus analyzes the second moving image, to acquire a second phase parameter indicating phase information regarding the motion of the organ in time phase images in the second moving image (still images at clock times (in time phases) included in the second moving image).

Next, based on the acquired first and second phase parameters, the image processing apparatus associates time phase images in which the pieces of phase information regarding the motion of the organ are similar to each other, between the first and second moving images. Then, the image processing apparatus combines the time phase images in the first and second moving images that are associated with each other as those in the same phase, to generate a combined image in this phase. The image processing apparatus thus generates combined images in a plurality of time phases and consequently can acquire images including the entire region of the observation target in the plurality of time phases. The image processing apparatus thus acquires deformation information on between the plurality of time phases of the combined images, whereby a degree of slippage near the contour of the entire region of the observation target can be calculated and displayed. This enables a user to observe the combined images including the entire region of the observation target and the degree of slippage.

With reference to FIGS. 1 to 5, the configuration and the processing of the present exemplary embodiment are described below. In the present exemplary embodiment, a description will be given using, as examples, three-dimensional moving images (four-dimensional computed tomography (CT) images) obtained by capturing a respiratory movement of lungs using an X-ray CT apparatus. The implementation of the image processing apparatus according to the present invention, however, is not limited to this. Alternatively, moving images obtained by capturing any part that makes a voluntary motion, such as a heart, may be used. Yet Alternatively, moving images obtained by capturing any part of a subject who makes a periodic movement (e.g., performs bending and stretching exercises) may be used.

FIG. 1 illustrates the configuration of the image processing apparatus according to the present exemplary embodiment. As illustrated in FIG. 1, an image processing apparatus 10 according to the present exemplary embodiment is connected to a data server 11 and a display unit 12.

The data server 11 holds a first moving image and a second moving image specified by a user as a target with which a degree of slippage is to be calculated. The first and second moving images are moving images including three-dimensional tomographic images in a plurality of time phases (also termed three-dimensional moving images or four-dimensional images) obtained in advance by capturing different image capturing ranges of the same subject using the same modality. The modality for capturing the three-dimensional tomographic images may be a magnetic resonance imaging (MRI) apparatus, an X-ray CT apparatus, a three-dimensional ultrasonic imaging apparatus, a photoacoustic tomography apparatus, a positron emission tomography (PET) apparatus, a single-photon emission computed tomography (SPECT) apparatus, or an optical coherence tomography (OCT) apparatus. The first and second moving images are input to the image processing apparatus 10 via a data acquisition unit 110.

The display unit 12 is a monitor that displays an image generated by the image processing apparatus 10.

The image processing apparatus 10 includes the following components. The data acquisition unit 110 acquires the first and second moving images input to the image processing apparatus 10. An extraction unit 115 extracts the region of a target organ in time phases of the first and second moving images. A phase parameter calculation unit 120 acquires a first phase parameter indicating phase information regarding a motion of an organ in the time phases of the first moving image, and a second phase parameter indicating phase information regarding the motion of the organ in the time phases of the second moving image. Based on the first and second phase parameters, a time phase association information acquisition unit 130 acquires time phase association information regarding the time phases of the first and second moving images. That is, the time phase association information acquisition unit 130 associates each of time phase images (a first time phase image) in the first moving image with a corresponding one of time phase images (a second time phase image) in the second moving image. A combining position acquisition unit 140 acquires a combining position between the first and second time phase images associated with each other as those in the same phase. A combined image generation unit 150 generates a combined image obtained by combining the first and second time phase images based on the combining position. Regarding combined images generated in a plurality of time phases, a deformation information estimation unit 160 acquires deformation information on between the plurality of time phases. Based on the deformation information, a degree-of-slippage calculation unit 170 calculates a degree of slippage near the contour of the entire region of the organ as the observation target. A display control unit 180 performs display control for displaying the first and second moving images and the degree of slippage on the display unit 12.

The above components of the image processing apparatus 10 function according to a computer program. For example, the functions of the components are achieved by a central processing unit (CPU) loading the computer program stored in a read-only memory (ROM) or a storage unit into a random-access memory (RAM) as a work area and executing the computer program. The functions of some or all of the components of the image processing apparatus 10 may be achieved using dedicated circuits. The functions of some of the components of the CPU may be achieved using a cloud computer.

For example, the functions of the components of the image processing apparatus 10 or a control unit may be achieved by the image processing apparatus 10 and a calculation apparatus transmitting and receiving data to and from each other. The calculation apparatus is disposed at a location different from that of the image processing apparatus 10 and connected to the image processing apparatus 10 via a network so that the calculation apparatus can communicate with the image processing apparatus 10.

Next, with reference to FIG. 2, an example of the processing of the image processing apparatus 10 in FIG. 1 is described.

FIG. 2 illustrates a flowchart of an entire processing procedure performed by the image processing apparatus 10.

(Step S200) (Acquisition of Data)

In step S200, the data acquisition unit 110 acquires a first moving image and a second moving image obtained by capturing a target object from positions different from each other using the imaging apparatus and input to the image processing apparatus 10. That is, step S200 corresponds to an example of a moving image acquisition step of acquiring a first moving image and a second moving image obtained by capturing a target object from positions different from each other using an imaging apparatus. Specifically, for example, in a case where the observation target is lungs, the data acquisition unit 110 acquires a first moving image and a second moving image obtained by capturing the lungs in a divided manner in the craniocaudal direction so that at least a partial region of the lungs is duplicate. That is, the first moving image is an image including an apical portion of the lungs, and the second moving image is an image including a bottom portion of the lungs. The observation target is not limited to the lungs, and for example, may be a heart, in which presence or absence of a disease appears in the motion of the organ similarly to lungs, or may be another organ.

Then, the data acquisition unit 110 outputs the acquired first and second moving images to the extraction unit 115, the phase parameter calculation unit 120, the combining position acquisition unit 140, and the combined image generation unit 150.

(Step S205) (Extraction of Organ Region)

In step S205, the extraction unit 115 extracts a region of the target organ in the time phases of the first and second moving images. Then, the extraction unit 115 outputs information regarding the extracted region of the target organ to the phase parameter calculation unit 120, the combining position acquisition unit 140, and the degree-of-slippage calculation unit 170.

A known image processing technique can be used for the process of extracting a region of an organ from images. Any threshold process using a threshold for a pixel value or a known segmentation process, such as a graph cut process, may be used. a region of a target organ may be manually extracted by the user using figure drawing software (not illustrated), or a region obtained by the user manually correcting the region of the target organ extracted using a known image processing technique may be used.

(Step S210) (Calculation of Phase Parameters)

In step S210, the phase parameter calculation unit 120 analyzes the first moving image, to calculate a first phase parameter indicating phase information regarding a periodic movement of the target organ. The phase parameter calculation unit 120 also analyzes the second moving image, to calculate a second phase parameter indicating phase information regarding the periodic movement of the target organ. The periodic movement of the target organ is, for example, a respiratory movement of lungs or a pulsation of a heart.

That is, the phase parameter calculation unit 120 corresponds to an example of a phase acquisition unit configured to acquire a first phase parameter indicating phase information regarding a motion of the target object in time phases of the first moving image, and a second phase parameter indicating phase information regarding a motion of the target object in time phases of the second moving image. Particularly, the phase parameter calculation unit 120 acquires the first phase parameter, based on a state of the target object captured in the first moving image, and acquires the second phase parameter, based on a state of the target object captured in the second moving image.

Then, the phase parameter calculation unit 120 outputs the calculated first and second phase parameters to the time phase association information acquisition unit 130.

In the present exemplary embodiment, the phase parameter calculation unit 120 calculates, as the first phase parameter, a numerical value correlated to the periodic movement of the target organ from time phase images (still images in time phases) included in the first moving image. For example, in a case where the target organ is the lungs, the volume of the lungs changes in conjunction with the respiratory movement. Thus, using the region of the lungs extracted in step S205, the phase parameter calculation unit 120 measures the volume of the lungs included in the time phase images and sets the magnitude of the volume of the lungs in the time phase images as the first phase parameter. Alternatively, the phase parameter calculation unit 120 may set a magnitude of an area of the lungs in a predetermined slice plane as the first phase parameter. It is known that in a CT image, the pixel value of an air region in the region of the lungs changes according to the volume of the lungs. Thus, the first phase parameter may be calculated, based on pixel value distribution information in the region of the lungs included in the time phase images. Alternatively, not only information that can be acquired from the lungs, but also information regarding a peripheral part that works in conjunction with the respiratory movement may be used. For example, the first phase parameter may be calculated based on the motion of the body surface of the chest and the abdomen or another organ. Further, the first phase parameter may be calculated by integrating a plurality of pieces of information that works in conjunction with the respiratory movement.

Similarly to the first phase parameter, the second phase parameter is also acquired by analyzing the second moving image using various methods. The first and second phase parameters, however, may not necessarily need to be calculated using the same method.

A configuration in which a phase parameter can be acquired from an external apparatus (not illustrated) may also be employed. For example, in a case where the target organ is lungs, a tidal volume of the subject may be measured using a spirometer simultaneously with the capturing of a moving image, and the measured value may be set as a phase parameter. Alternatively, a motion of a body surface of the subject when a moving image is captured may be measured using a laser sensor or a pressure sensor, and the measured value may be set as a phase parameter.

(Step S220) (Acquisition of Time Phase Association Information)

In step S220, based on the first and second phase parameters, the time phase association information acquisition unit 130 associates time phase images in the first and second moving images having similar phases to each other, and acquires information used in the association as time phase association information. The time phase association information is information indicating which time phase of the first moving image is the most similar to which time phase of the second moving image.

That is, time phase association information acquisition unit 130 corresponds to an example of an association unit configured to associate, based on the first and second phase parameters, time phase images obtained from the first moving image and time phase images obtained from the second moving image. Particularly, the time phase association information acquisition unit 130 associates time phase images having the first phase parameter and the second phase parameter similar to each other.

The time phase association information is specifically described using a case as an example where the target organ is lungs, and the first and second phase parameters are calculated based on a volume of the lungs. Since the first and second moving images include different regions of the lungs, even if the volume of the lungs is similar between the first and second moving images, a tidal volume is not necessarily similar between the first and second moving images. Thus, for example, the first phase parameter is calculated by normalizing the first phase parameter so that the value of the first phase parameter at the maximal inspiratory level at which the volume of the lungs in the first moving image reaches a maximum is 1, and the value of the first phase parameter at the maximal expiratory level at which the volume of the lungs reaches a minimum is 0. Similarly, the second phase parameter is also calculated by normalizing the second phase parameter so that the second phase parameter is in the range from 0 to 1.

Consequently, a predetermined time phase image having the normalized first phase parameter in the first moving image and a predetermined time phase image having the normalized second phase parameter similar to the normalized first phase parameter in the second moving image can be associated with each other. Then, a pair of the time phase image in the first moving image and the time phase image in the second moving image that are thus associated with each other is acquired as the time phase association information.

Specifically, for example, the time phase association information acquisition unit 130 associates time phase images at the maximal inspiratory level in the first and second moving images, in which numerical values of the normalized first phase parameter and the normalized second phase parameter are 1, and acquires a pair of the time phase image at the maximal inspiratory level in the first moving image and the time phase image at the maximal inspiratory level in the second moving image as a piece of time phase association information. Then, the time phase association information acquisition unit 130 associates time phase images at the maximal expiratory level in the first and second moving images, in which the numerical values of the normalized first phase parameter and the normalized second phase parameter are 0, and acquires a pair of the time phase image at the maximal expiratory level in the first moving image and the time phase image at the maximal expiratory level in the second moving image as a piece of time phase association information.

That is, the time phase association information acquisition unit 130 associates a time phase image having the first phase parameter at a maximum value and a time phase image having the second phase parameter at a maximum value, and also associates a time phase image having the first phase parameter at a minimum value and a time phase image having the second phase parameter at a minimum value. Then, also in phases other than those of the maximal inspiratory level and the maximal expiratory level, similarly, the time phase association information acquisition unit 130 associates a first time phase image and a second time phase image having the similar phase parameters to each other.

Figure 3A:
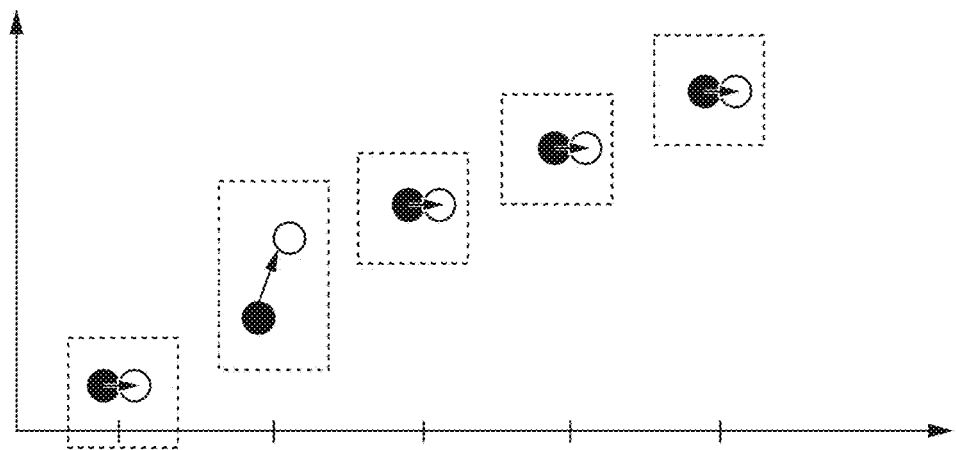
FIGS. 3A, 3B and 3C is diagrams each illustrating an example of association between a first moving image and a second moving image according to the first exemplary embodiment.
Figure 3B:
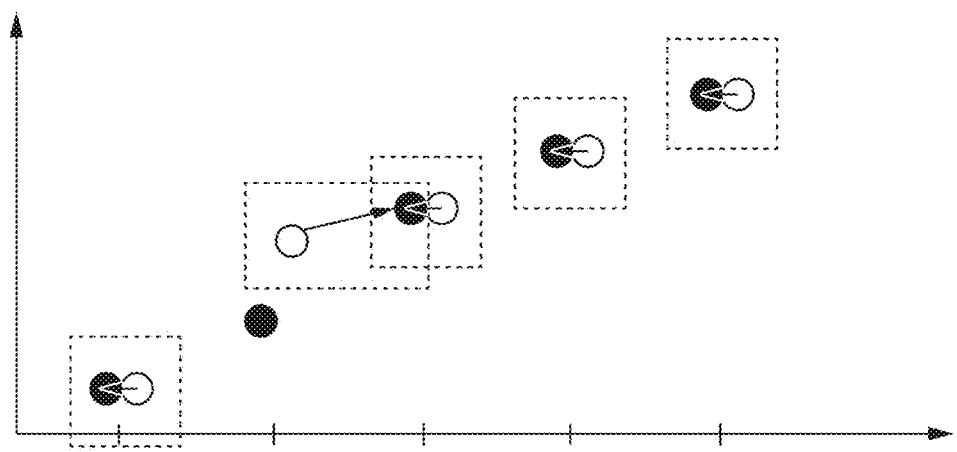
Figure 3C:
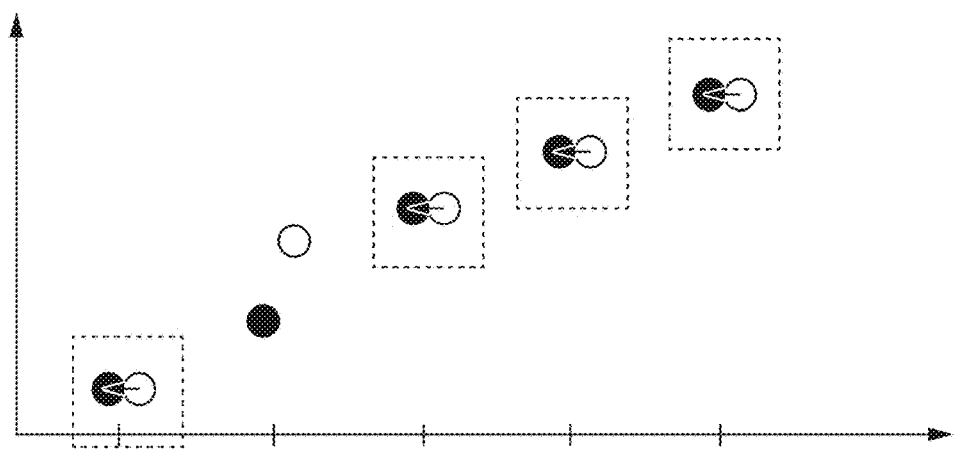

Next, FIGS. 3A to 3C illustrate specific examples of the result of associating a plurality of time phase images using normalized phase parameters. In FIGS. 3A to 3C, when the horizontal axis represents time, and the vertical axis represents a phase parameter, the first phase parameter as a black point and the second phase parameter as a white point are arranged from the left in time phase order.

An example where the number of time phases of the first and second moving images is five is taken. The first phase parameter is {0.0, 0.3, 0.6, 0.8, 1.0} in order from the first time phase, and the second phase parameter is {0.0, 0.5, 0.6, 0.8, 1.0} in order from the first time phase.

As illustrated in FIG. 3A, in a case where a time phase image having the first phase parameter as a reference is associated with a time phase image in a time phase of the second phase parameter that is the most similar to the time phase image having the first phase parameter, time phase images in the first and second moving images result in being associated with each other on a one-to-one basis in order from the first time phase, and the number of time phases in which time phase images are associated with each other is five.

As illustrated in FIG. 3B, in a case where the second phase parameter is used as a reference, both time phase images in the second time phase (0.5) and the third time phase (0.6) of the second phase parameter are associated with a time phase image in the third time phase (0.6) of the first phase parameter, and the number of time phases in which time phase images are associated with each other is five.

In a case where both the values of one of the phase parameters in a plurality of time phases are the most similar to the value of the other phase parameter in the same time phase, only a single pair of time phase images having the most similar phase parameters may be associated with each other. In this case, the time phase image in the other time phase that is not associated may be associated with a time phase image in the second time phase or later in which the phase parameter is similar to that of the time phase image in the other time phase, or may not be associated and used in the subsequent steps.

That is, as illustrated in FIG. 3C, in a case where time phase images that are not associated with each other in a time phase are not used in the subsequent steps, and in a case where the second phase parameter is used as a reference, time phase images in the second time phase of the first and second phase parameters are not associated with each other, and the number of time phases in which time phase images are associated with each other is four.

As described above, using normalized parameters, a plurality of time phase images obtained from the first moving image and a plurality of time phase images obtained from the second moving image can be associated with each other.

The number of phase parameters and the number of pairs of time phase images associated with each other in the above example are merely illustrative, and are not limited to the above.

Time phase images in time phases may be associated with each other, based on the first and second phase parameters without normalizing the first and second phase parameters. For example, in a case where the first and second phase parameters are calculated using approximately the same part of the subject between the first and second moving images, time phase images in time phases in which the phase parameters are similar can be associated with each other as time phase images in time phases similar in the tidal volume without normalizing the phase parameters. Specifically, using an apparatus coordinate system that can be acquired from header information regarding a moving image, the positions of the body surface of the chest and the abdomen at the same position in the apparatus coordinate system on the first and second moving images are acquired as the first and second phase parameters, respectively. In this case, time phase images in time phases in which the phase parameters are similar (the positions of the body surface are close) between the first and second moving images may be associated with each other without normalizing the phase parameters.

Hereinafter, the maximal inspiratory level will be referred to as a "reference phase", and the maximal expiratory level will be referred to as a "comparison phase". Time phase images in the first and second moving images that are associated with each other at the maximal inspiratory level as the reference phase will be referred to as a "first reference image" and a "second reference image", respectively. Time phase images in the first and second moving images that are associated with each other at the maximal expiratory level as the comparison phase will be referred to as a "first comparison image" and a "second comparison image", respectively. Alternatively, the maximal expiratory level may be set as the reference phase, and the maximal inspiratory level may be set as the comparison phase. Yet alternatively, another phase acquired from each of the first and second moving images may be assigned as the reference phase or the comparison phase.

(Step S230) (Calculation of Combining Position Information)

In step S230, in each of the time phases in which the time phase images are associated with each other in step S220, the combining position acquisition unit 140 calculates, as combining position information, the position where the first time phase image obtained from the first moving image and the second time phase image obtained from the second moving image are to be combined together. That is, the combining position acquisition unit 140 corresponds to an example of a combining position information acquisition unit configured to acquire combining position information between a first reference image obtained from the first moving image and a second reference image obtained from the second moving image. Then, the combining position acquisition unit 140 outputs the calculated combining position information to the combined image generation unit 150.

As the combining position, a position on the second time phase image corresponding to a predetermined position on the first time phase image is calculated. For example, when an i-th slice position on the first time phase image is P1_i, a j-th slice position P2_j on the second time phase image corresponding to the slice position P1_i on the first time phase image is searched for. Then, the slice position P2_j on the second time phase image corresponding to the slice position P1_i on the first time phase image is held as the combining position. It is desirable to select the slice position P1_i from within a duplicate region between the first and second moving images. As the combining position, the positions of pixels on the second time phase image corresponding to pixels on the slice position P1_i on the first time phase image may be calculated instead of a slice position.

The combining position can be calculated using a known image processing technique by searching for a position so that pixels indicating the same position between the first and second time phase images approximately match each other. For example, a slice position is searched for such that the similarity between images is high between tomographic images at predetermined slice positions. As the similarity between images, any of known methods, such as the sum of squared differences (SSD), mutual information, and a cross-correlation coefficient, which are generally used, can be employed.

Not only the combining position but also the reliability of the combining position can be calculated as the combining position information. The motion of the lungs in the craniocaudal direction from the reference phase to the comparison phase is made in approximately a single direction. In a case where the slice position P2_j corresponding to the slice position P1_i in the time phases is searched for, the value of j is expected to monotonically change in a single direction or hardly change when i is a fixed value. That is, for example, in a case where the indicated combining position is greatly different from other time phases only in a certain single time phase, it is likely that the result of calculating the combining position in this time phase is incorrect. Thus, it can be determined that the reliability of the combining position is low. As the reliability of the combining position, a value based on a value of the second derivative of the combining position calculated in consecutive time phases, e.g., a value inversely proportional to the value of the second derivative (a value proportional to the level of the reliability), can be used. That is, the combining position acquisition unit 140 corresponds to an example of a calculation unit configured to calculate a reliability of a combining position of a time phase image obtained from the first moving image and a time phase image obtained from the second moving image that are associated with each other by the association unit.

(Step S240) (Generation of Combined Image)

In step S240, based on the combining position in each of the time phases calculated in step S230, the combined image generation unit 150 generates a combined image obtained by combining the first and second time phase images. Then, the combined image generation unit 150 outputs the generated combined image to the deformation information estimation unit 160 and the display control unit 180.

Based on the combining position calculated in step S230, the combined image generation unit 150 combines the first and second time phase images so that a position on the first time phase image and a position on the second time phase image corresponding to the position on the first time phase image overlap each other, to generate a combined image. With reference to FIG. 4, this process is specifically described. In FIG. 4, an image 400 represents a coronal section of the first time phase image, and a dashed line 410 indicates the slice position P1_i. An image 420 represents a coronal section of the second time phase image, and a dashed line 430 indicates the slice position P2_j corresponding to the slice position P1_i and calculated in step S230.

Then, an image 440 represents a combined image obtained by translating the second time phase image in the slice direction so that the slice position P1_i on the first time phase image and the slice position P2_j on the second time phase image overlap each other, and combining the first and second time phase images. A region 450 indicates a region captured in only the first time phase image. A region 460 indicates a region captured in both the first and second time phase images. A region 470 indicates a region captured in only the second time phase image. Each of the pixel values of the combined image in the regions 450 and 470 is the pixel value of one of the first and second time phase images. The pixel value of the combined image in the region 460 may be either one of the pixel values of the first and second time phase images, or may be the average value of the pixel values of the first and second time phase images. A weighted average value may be used where according to the position in the region 460, the weight of the pixel value of the first time phase image is greater at a pixel closer to the apical portion of the lungs, and the weight of the pixel value of the second time phase image is greater at a pixel closer to the bottom portion of the lungs.

In the present exemplary embodiment, based on the reliability of the combining position calculated in step S230, it may be determined whether a combined image is to be generated. In a case where the reliability of the combining position is calculated, it may be determined whether the reliability of the combining position is greater than or equal to a predetermined threshold set in advance. Then, only if the reliability of the combining position is greater than or equal to the threshold, it may be determined that the reliability of the combining position is high, and a combined image may be generated. In other words, among the pairs of time phase images associated with each other in step S220, a pair of time phase images in which the calculated reliability of the combining position is greater than or equal to the predetermined threshold may be selected, and a combined image may be generated. A pair of time phase images to generate a combined image may be selected by the user, or may be automatically selected based on the reliability.

That is, the combined image generation unit 150 corresponds to an example of a generation unit configured to generate a combined image by selecting at least two or more pairs of time phase images in which the reliability is greater than or equal to a threshold.

Consequently, it is possible to reduce the possibility of generating a combined image in which combining positions are not aligned. By using only a combined image having a high reliability, it is possible to calculate the degree of slippage with high accuracy in the subsequent processes.

In the present exemplary embodiment, a combined image is generated by translating the second time phase image so that the slice position P1_i on the first time phase image and the slice position P2_j on the second time phase image corresponding to the slice position P1_i on the first time phase image overlap each other. The method for generating a combined image, however, is not limited to this. For example, in a case where not the slice positions but the positions of pixels are calculated as the combining position information, the first and second time phase images may be combined together by deforming the second time phase image so that the pixels overlap each other at the combining position. In a case where a combined image is generated by translating the second time phase image so that the slice position P1_i on the first time phase image and the slice position P2_j on the second time phase image corresponding to the slice position P1_i on the first time phase image overlap each other, the first and second time phase images may be combined together after deforming the second time phase image so that predetermined parts, such as the positions of the body surface and the positions of a bronchus branch, match each other.

Consequently, it is possible to generate combined images in a plurality of time phases. That is, it is possible to acquire combined images in time series including the entire region of the observation target. Hereinafter, a combined image obtained by combining the first and second reference images in the reference phase will be referred to as a "reference combined image" (or a "first combined image"). A combined image obtained by combining the first and second comparison images in the comparison phase will be referred to as a "comparison combined image" (or a "second combined image").

(Step S250) (Estimation of Deformation Information)

In step S250, the deformation information estimation unit 160 performs registration between the combined images in the plurality of time phases and estimates deformation information indicating the time-series deformation of the subject. Then, the deformation information estimation unit 160 outputs the estimated deformation information to the degree-of-slippage calculation unit 170.

In the present exemplary embodiment, the deformation information is obtained by a known image processing technique. For example, the deformation information is obtained by deforming one of images so that the similarity between the images after the deformation is high. As a deformation model for the image, a deformation model based on a radial basis function such as a thin plate spline (TPS) or a known deformation model based on free-form deformation (FFD) can be used.

The deformation information may be estimated such that anatomical feature points approximately match each other, instead of using the similarity between images. For example, feature points may be set in a bronchus branch or a blood vessel branch inside the region of the lungs, and a rib or a breast bone outside the region of the lungs, and the amounts of movement of the feature points may be estimated as the deformation information.

With the deformation information, registration is performed between all combined images in time phases adjacent to each other, to estimate a time-series motion between the reference combined image, which is the combined image in the reference phase, and the comparison combined image, which is the combined image in the comparison phase. For example, in step S240, in a case where at least one of the reference combined image and the comparison combined image is set as a combined image in another time phase different from the reference phase and the comparison phase, a target for which a time-series motion is to be estimated is not limited to the time series between the reference combined image and the comparison combined image.

Consequently, even in a case where deformation is large between the reference phase and the comparison phase, deformation is small between combined images in time phases adjacent to each other. This facilitates the registration process. Meanwhile, the processing time required for the registration process increases in proportion to the number of time phases. Thus, the deformation information may be estimated using only some time phases obtained by thinning out time phases at predetermined intervals. The deformation between the reference combined image and the comparison combined image may be directly obtained. The deformation information is represented by, for example, a displacement vector field from the reference combined image to the comparison combined image.

In the present exemplary embodiment, based on the reliability of the combining position calculated in step S230, a combined image to be used to estimate the deformation information may be selected. In a case where the combining position is incorrect, there is a possibility that anatomical inconsistency occurs near the combining position of the combined image. Thus, in a case where the reliability of the combining position is calculated, it is determined whether the reliability of the combining position is greater than or equal to a predetermined threshold set in advance. Then, only if the reliability of the combining position is greater than or equal to the threshold, the combined image is selected as an image to be used to estimate the deformation information, and thus it is possible to estimate the deformation information with high accuracy.

In this case, in a case where at least one combined image is thinned out based on the reliability, the deformation information cannot be estimated unless there are two or more combined images, and therefore, it is desirable to generate three or more combined images in step S240.

That is, the deformation information estimation unit 160 selects two or more combined images in which the reliability is greater than or equal to the threshold from among the three or more combined images, and estimates the deformation information, based on the selected combined images.

In a case where a combined image is not necessarily thinned out, the number of combined images to be generated in step S240 may be two.

Consequently, it is possible to estimate the deformation information using only combined images having a high reliability. Thus, it is possible to calculate a degree of slippage with high accuracy in the subsequent processes.

(Step S260) (Calculation of Degree of Slippage)

In step S260, based on the deformation information estimated in step S250, the degree-of-slippage calculation unit 170 calculates a degree of slippage at each position near the contour of the target organ. That is, the degree-of-slippage calculation unit 170 corresponds to an example of a degree-of-slippage calculation unit configured to calculate a degree of slippage of the target object, based on deformation information estimated from the first and second combined images. Then, the degree-of-slippage calculation unit 170 outputs the calculated degree of slippage to the display control unit 180.

Figure 5:
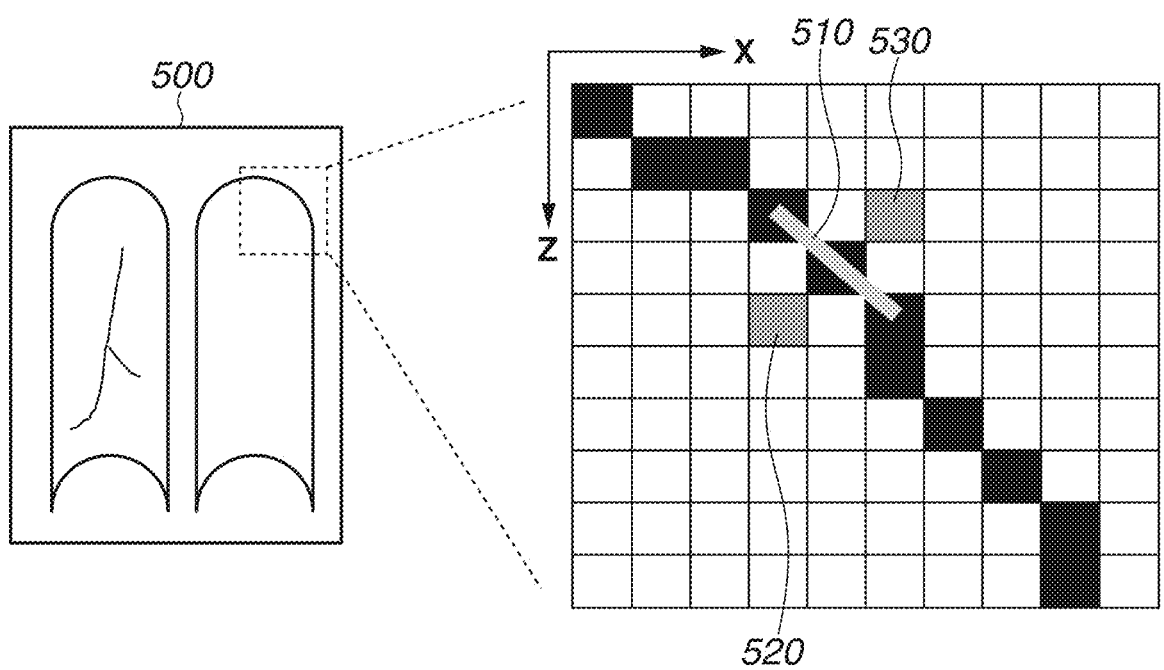
FIG. 5 is a diagram illustrating an example of setting of reference points according to the first exemplary embodiment.

In the present exemplary embodiment, a degree of slippage is obtained by calculating to what degree a pixel near the contour of the target organ inside the region of the target organ extracted in step S205 slips relative to neighboring pixels outside the region of the target organ. For example, as illustrated in FIG. 5, two pixels, namely a pixel 520 inside the region of the lungs and a pixel 530 outside the region of the lungs that are adjacent to each other in a direction normal to a contour line 510 of the region of the lungs in a combined image 500 in the reference phase (the reference combined image), are set as reference points. Then, a norm of the difference in the deformation information (a vector) between the combined image in the reference phase (the reference combined image) and the combined image in the comparison phase (the comparison combined image) at the two set reference points can be calculated as a degree of slippage at this position in the target organ. That is, the degree of slippage corresponds to an example of a relative amount of movement between a reference point set inside a region of the lungs using a contour line as a reference and a reference point set outside the region of the lungs using the contour line as the reference. The norm of the difference in the deformation information may be a norm of the difference between vectors along the surface of the contour of the lungs. The number of reference points to be set is merely illustrative, and is not limited to the above. Further, one of two reference points corresponding to each other may be set on the contour line. Further, a degree of slippage may not necessarily need to be obtained from the deformation information between the reference phase and the comparison phase, and deformation information calculated from time phase images in any phase between the reference phase and the comparison phase can be used. The method for calculating a degree of slippage is not limited to this, and a known image processing technique may be used.

(Step S270) (Display of Degree of Slippage)

In step S270, the display control unit 180 visualizes the degree of slippage calculated in step S260 and displays the degree of slippage on the display unit 12.

As the method for visualizing the degree of slippage, a degree-of-slippage map can be generated and displayed on the display unit 12. The degree-of-slippage map is, for example, an image in which a pixel at a contour position of the lungs is set to a gray scale value or a color scale value according to the degree of slippage as a pixel value. The degree-of-slippage map may be displayed in parallel with or in a superimposed manner on the combined image in the reference phase (the reference combined image). The degree-of-slippage map may be displayed in parallel with or in a superimposed manner on a combined image in a phase other than the reference phase. In this case, it is desirable to perform coordinate transformation on the degree-of-slippage map so that the degree-of-slippage map is positionally consistent with the combined image in the phase other than the reference phase. The degree-of-slippage map may be displayed in parallel with or in a superimposed manner on combined images in a plurality of time phases. Further, the combined images may be displayed as a moving image obtained by continuously switching the combined images. Further, the degree-of-slippage map may be displayed in parallel with or in a superimposed manner on the first moving image or the second moving image as an input image. Also in this case, it is desirable to display the degree-of-slippage map such that the degree-of-slippage map is spatially consistent with the first moving image or the second moving image. The process of displaying the degree of slippage is not necessarily required. Alternatively, a configuration may be employed in which information regarding the degree of slippage calculated in step S260 is output to and saved in the data server 11.

Based on the above, the processing of the image processing apparatus 10 is performed.

According to the above, since combined images in a plurality of time phases including the entire region of an observation target are generated, and registration is performed between the combined images in the time phases, it is possible to calculate the degree of slippage near the contour of the entire region of the observation target with high accuracy. More specifically, in a case where two reference points to be set across a contour line are set near the boundary between moving images, the positions of the reference points after the phase changes may not fall within the image capturing range. For example, in a case where the lungs are captured using a CT apparatus, since the sensor size of the CT apparatus is about the size of a heart, lungs need to be captured by dividing the lungs into upper and lower portions in the craniocaudal direction to capture the entire region of the lungs, which are greater in volume than the heart. Thus, in a case where images captured in a divided manner are combined together at the boundary between the images, it is difficult to calculate a degree of slippage near the boundary as the combining target.

According to the above, however, a plurality of moving images obtained by capturing the region of an organ in a divided manner is combined together, thus the positions of reference points after the phase changes fall within any combined image. Consequently, even in a case where two reference points are set near the boundary between moving images, it is possible to calculate the degree of slippage based on deformation information with high accuracy. Then, the user can observe combined images including the entire region of the observation target and the degree of slippage. According to the above, it is possible to calculate the degree of slippage of the entire region of the observation target (the lungs) with high accuracy. Thus, it is possible to reduce the possibility that the user erroneously recognizes an adhesion.

(Variation 1-1)

In the present exemplary embodiment, in step S230, the single slice position P2_j on the second time phase image corresponding to the slice position P1_i on the first time phase image is calculated. The slice position to be calculated, however, may not necessarily be a single position.

In the respiratory movement of lungs, the direction of the motion is different between inside the region of the lungs and outside the region of the lungs. Thus, in a case where the slice position P2_j on the second time phase image corresponding to the slice position P1_i on the first time phase image is searched for using the similarity between images, the combining position may be able to be correctly calculated in one of the inside of the region of the lungs and the outside of the region of the lungs, but may not be correctly calculated in the other. Thus, using the region of the lungs extracted in step S205, a combining position may be searched for in each of the inside of the region of the lungs and the outside of the region of the lungs. In this case, a slice position P2_k on the second time phase image in which the similarity between images inside the region of the lungs is high with the slice position P1_i on the first time phase image, and a slice position P2_1 in which the similarity between images outside the region of the lungs is high with the slice position P1_i on the first time phase image are set as the combining positions. In this case, in step S240, a combined image combined at each combining position can be generated. That is, two combined images obtained by combining the first and second time phase images at the combining positions inside the region of the lungs and outside the region of the lungs are generated in each of the time phases. Then, in step S250, deformation information regarding the combined images at each combining position is estimated. Regarding the deformation information estimated in each of the inside of the region of the lungs and the outside of the region of the lungs, the deformation information estimated using the combined images in all the portions inside the region of the lungs and the deformation information estimated using the combined images in all the portions outside the region of the lungs may be integrated into a single piece of deformation information using the region of the lungs extracted in step S205. Then, in step S260, based on the deformation information estimated inside the region of the lungs and the deformation information estimated outside the region of the lungs, a degree of slippage at each position near the contour of the target organ is calculated. Or based on the deformation information obtained by integrating the deformation information estimated inside the region of the lungs and the deformation information estimated outside the region of the lungs, a degree of slippage at each position near the contour of the target organ is calculated.

Consequently, it is possible to generate combined images from time phase images having the highest similarity inside and outside the region of an organ as an observation target. Thus, it is possible to calculate a degree of slippage with higher accuracy.

(Variation 1-2)

In the present exemplary embodiment, in step S250, in a case where deformation information is estimated between the combined images in the plurality of time phases, the deformation information may be estimated in each of the inside of the region of the lungs and the outside of the region of the lungs. That is, the degree-of-slippage calculation unit 170 may calculate a degree of slippage of the target object, based on deformation information inside the target object and deformation information outside the target object that are estimated from the first and second combined images. For example, in a case where deformation information is estimated between combined images combined at combining positions inside the region of the lungs, the deformation information may be estimated by performing preprocessing such as pixel value conversion on the combined images into conditions suitable for the observation of the inside of the region of the lungs (e.g., a window level (WL) of −600 and a window width (WW) of 1500). In a case where deformation information is estimated between combined images combined at combining positions outside the region of the lungs, the deformation information may be estimated by performing preprocessing such as pixel value conversion on the combined images into conditions suitable for the observation of the outside of the region of the lungs (e.g., a WL of 60 and a WW of 400).

Consequently, it is possible to estimate deformation information, based on conditions suitable for the observation of the inside and the outside of the region of an organ as an observation target. Thus, it is possible to calculate a degree of slippage with higher accuracy.

(Variation 1-3)

In the present exemplary embodiment, in step S240, a combined image is generated. Alternatively, steps S230 to S250 may be replaced with the following process, to estimate deformation information without generating a combined image. First, the combining position acquisition unit 140 acquires relative position information regarding the first reference image included in the first moving image and the second reference image included in the second moving image as combining position information. Then, the deformation information estimation unit 160 estimates first deformation information between the first reference image and the first comparison image included in the first moving image and estimates second deformation information between the second reference image and the second comparison image included in the second moving image. Further, based on the combining position information, the deformation information estimation unit 160 estimates third deformation information between the first reference image and the second comparison image. Alternatively, the deformation information estimation unit 160 estimates deformation information between the first comparison image and the second reference image as the third deformation information. For example, deformation information regarding a part captured in common in the first reference image and the second comparison image can be calculated by integrating the combining position information and the second deformation information. The first deformation information, the second deformation information, and the third deformation information calculated by the above process are integrated together, whereby deformation information similar to the deformation information described in step S250 in the first exemplary embodiment is estimated. Specifically, for example, the first deformation information, the second deformation information, and the third deformation information can be integrated together using a common region such that deformation information regarding a region captured in common in the first reference image and the first comparison image is used as the first deformation information. In this case, the first deformation information, the second deformation information, and the third deformation information can be integrated together such that deformation information regarding a common region in the second reference image and the second comparison image is used as the second deformation information, and deformation information regarding a common region in the first reference image and the second comparison image is used as the third deformation information.

Consequently, a degree of slippage can be calculated without generating a combined image. Thus, it is possible to reduce a memory of a computer required to hold a combined image.

(Variation 1-4)

In the present exemplary embodiment, in step S240, combined images in a plurality of time phases are generated. Alternatively, steps S230 to S250 may be replaced with the following process, to estimate deformation information by generating a combined image in only a single time phase. Relative position information regarding the first and second reference images is acquired as combining position information, and based on the combining position information, a reference combined image obtained by combining the first and second reference images is generated. Then, fourth deformation information between the reference combined image and the first comparison image is estimated, and fifth deformation information between the reference combined image and the second comparison image is estimated. The fourth deformation information and the fifth deformation information calculated by the above process are integrated together, whereby deformation information similar to the deformation information described in step S250 in the first exemplary embodiment is estimated. Specifically, the fourth deformation information and the fifth deformation information can be integrated together such that deformation information regarding a common region in the reference combined image and the first comparison image is used as the fourth deformation information, and deformation information regarding a common region in the reference combined image and the second comparison image is used as the fifth deformation information.

Consequently, a combined image in only a single time phase is generated. Thus, it is possible to reduce a memory of a computer required to hold a combined image.

Second Exemplary Embodiment

In the first exemplary embodiment, time phase images associated with each other as those in the same phase between the first and second moving images are combined together, to generate a combined image. On the other hand, an image processing apparatus according to the present exemplary embodiment generates an interpolation image between time phase images as needed and generates a combined image using the interpolation image.

Specifically, for example, in a case where the second moving image does not include a time phase image having the second phase parameter similar to the first phase parameter of the first time phase image in the first moving image, an interpolation image having the phase corresponding to that of the first time phase image is generated from two time phase images included in the second moving image. Then, a combined image is generated from the first time phase image and the interpolation image.

Consequently, an interpolation image having the phase corresponding to that of the first time phase image can be generated from the second moving image. Thus, the user can observe a combined image obtained by combining time phase images having the phases corresponding to each other.

The following description is given of a case where, similarly to the first exemplary embodiment, an organ as the observation target is lungs, and the first and second moving images are four-dimensional CT images. The organ as the observation target and the imaging apparatus, however, are not limited to these.

Figure 6:
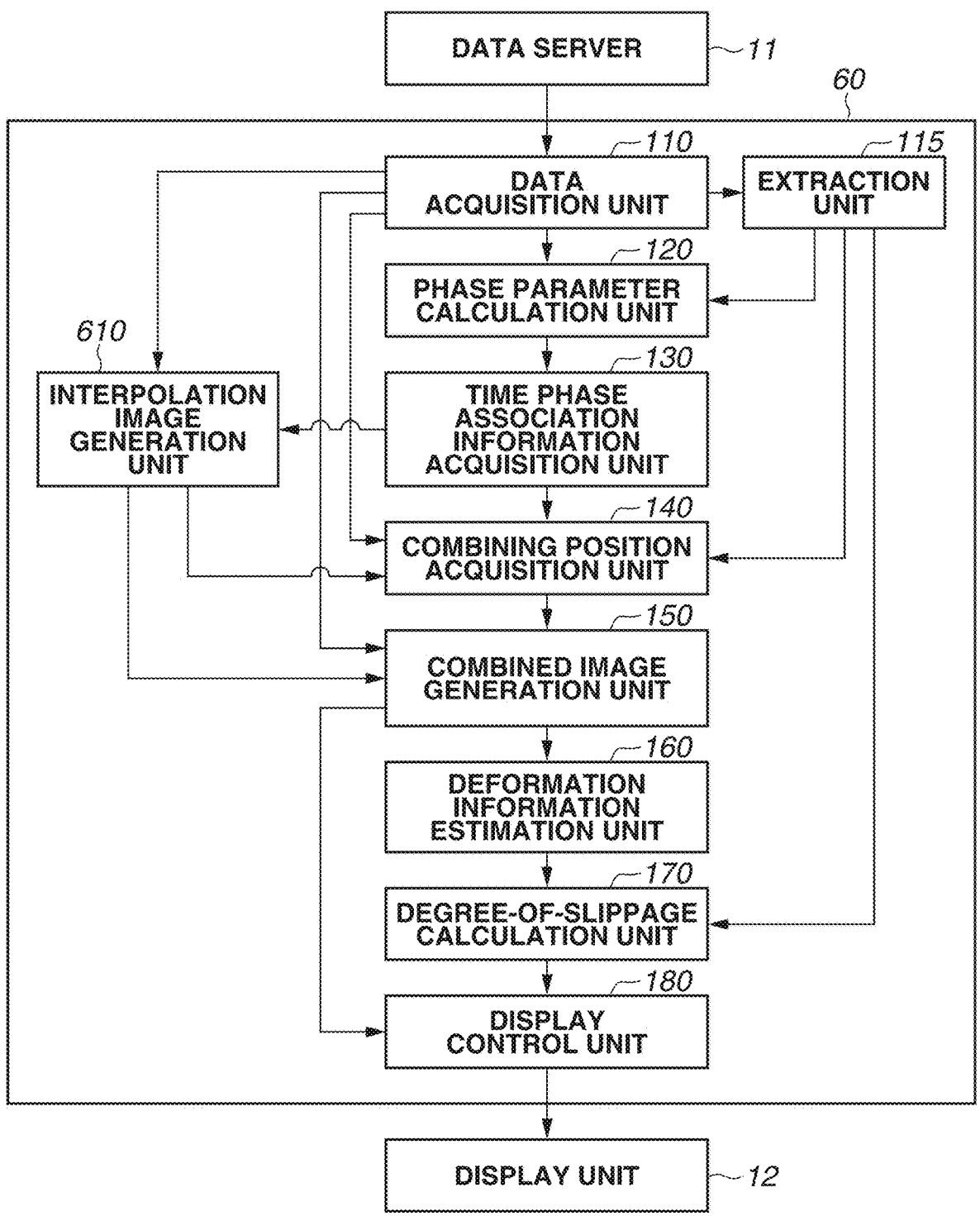
FIG. 6 is a diagram illustrating an example of a device configuration of an image processing apparatus according to a second exemplary embodiment.
Figure 7:
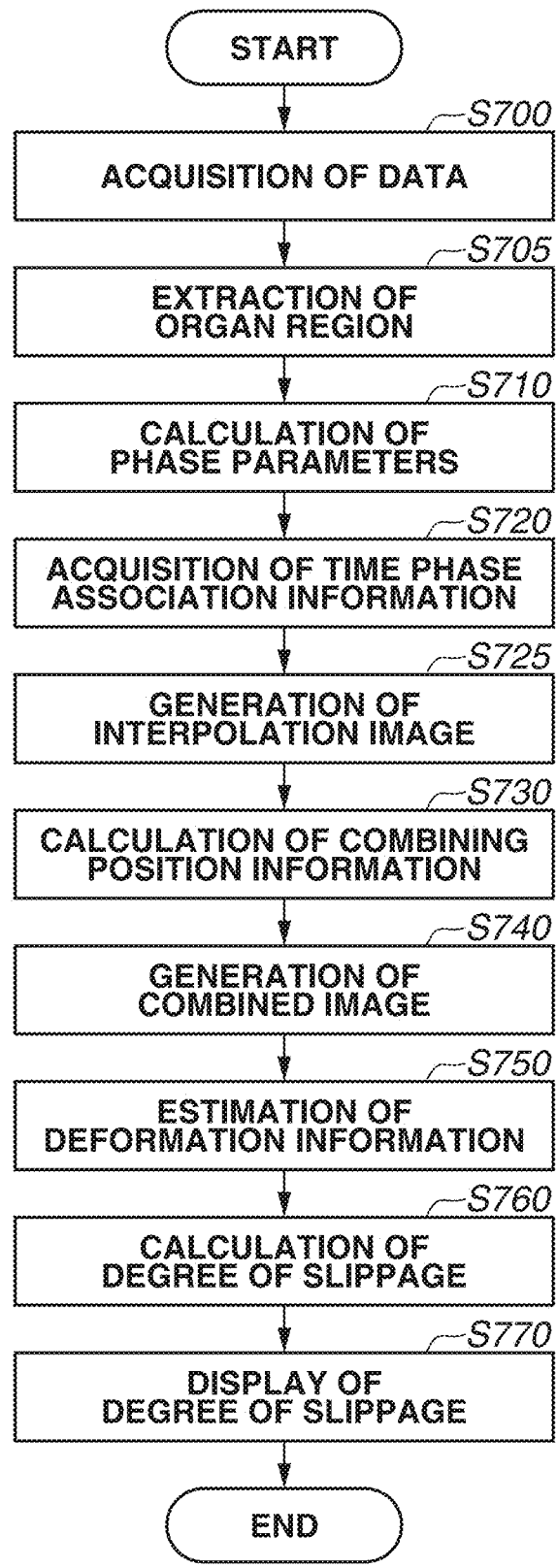
FIG. 7 is a flowchart illustrating an example of an entire processing procedure according to the second exemplary embodiment.
Figure 8:
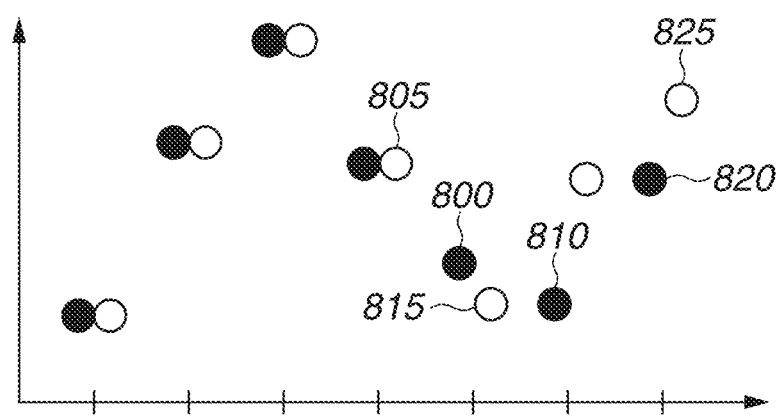
FIG. 8 is a diagram illustrating examples of phase parameters according to the second exemplary embodiment.

With reference to FIGS. 6 to 8, the configuration and the processing of the present exemplary embodiment are described below.

FIG. 6 illustrates the configuration of the image processing apparatus according to the present exemplary embodiment. The functions of the time phase association information acquisition unit 130 and an interpolation image generation unit 610 are described below. The functions of other components are similar to those in the first exemplary embodiment, and therefore are not described here.

The time phase association information acquisition unit 130 acquires an interpolation time phase of either one of the first and second moving images having a phase corresponding to that of a predetermined time phase image (the first time phase image) of the other. The interpolation time phase represents a time phase between consecutive time phases in which images are captured. The interpolation image generation unit 610 generates a time phase image (an interpolation image) corresponding to the interpolation time phase from a time phase image in another time phase.

FIG. 7 illustrates a flowchart of the entire processing procedure performed by an image processing apparatus 60. The processes of steps S700 to S710 and steps S730 to S770 are similar to those of steps S200 to S210 and steps S230 to S270, respectively, in the first exemplary embodiment, and therefore the redundant descriptions are omitted. Only the differences from the flowchart in FIG. 2 are described below.

(Step S720) (Acquisition of Time Phase Association Information)

In step S720, similarly to the process of step S220 in the first exemplary embodiment, the time phase association information acquisition unit 130 associates time phase images in the first and second moving images having the phases corresponding to each other, based on the first and second phase parameters. Then, the time phase association information acquisition unit 130 acquires information indicating the similarity between the phases as time phase association information. However, in the first and second moving images, a predetermined time phase image (to which attention is paid) does not include the time phase of the other phase parameter that matches that of the one phase parameter, the process of associating the time phase image with an interpolation time phase is performed.

With reference to FIG. 8, this process is specifically described. In FIG. 8, when the horizontal axis represents time, and the vertical axis represents a phase parameter, the first phase parameter as a black point and the second phase parameter as a white point are arranged from the left in time phase order. In a case where time phase images having similar phase parameters are associated with each other using the second phase parameter as a reference, a time phase image 800 in the fifth time phase of the first moving image is not associated with any of time phase images in the second moving image. In the present exemplary embodiment, an interpolation time phase to be associated with the time phase image 800 in the fifth time phase of the first moving image is acquired. For example, a time phase image in the fourth time phase of the first moving image and a time phase image 805 in the fourth time phase of the second moving image are associated with each other, and a time phase image 810 in the sixth time phase of the first moving image and a time phase image 815 in the fifth time phase of the second moving image are associated with each other. Based on this, it can be estimated that the time phase image 800 in the fifth time phase of the first moving image indicates the state of the subject between the time phase image 805 in the fourth time phase and the time phase image 815 in the fifth time phase of the second moving image. Thus, the time phase image 800 in the fifth time phase of the first moving image is associated with an interpolation time phase (e.g., the 4.5th time phase) between the time phase image 805 in the fourth time phase and the time phase image 815 in the fifth time phase of the second moving image. The interpolation time phase can also be calculated as follows.

For example, a case is considered where time phase images in an a-th time phase of the first moving image and a b-th time phase of the second moving image are associated with each other, and further, a time phase image in an a+c(0<c)-th time phase of the first moving image and a time phase image in a b+d(0<d)-th time phase of the second moving image are associated with each other. In this case, an interpolation time phase b+f(0<f<d) of the second moving image to be associated with a time phase image (0<e<c) in an a+e-th time phase of the first moving image can be acquired using the following formula (1):

$$b+f=b+d\times e/c \qquad (1).$$

The method for acquiring an interpolation time phase is not limited to the above method. For example, an interpolation time phase may be acquired based on values of phase parameters.

For example, a case is considered where a value of the first phase parameter of the time phase image in the a+e-th time phase of the first moving image is p_e, and values of the second phase parameter of the time phase images in the b-th time phase and the b+d-th time phase of the second moving image are p_b and p_d (p_b<p_e<p_d), respectively. In this case, the interpolation time phase b+f can be acquired using the following formula (2) according to ratios between the phase parameters:

$$b+f=b+d\times(p\_e-p\_b)/(p\_d-p\_b) \qquad (2).$$

In the present exemplary embodiment, a description has been given of the method for acquiring an interpolation time phase of the second moving image corresponding to a predetermined time phase image (to which attention is paid) in the first moving image. Alternatively, an interpolation time phase of the first moving image corresponding to a predetermined time phase image (to which attention is paid) in the second moving image may be acquired using a similar method.

(Step S725) (Generation of Interpolation Image)

In step S725, in a case where the interpolation time phase is acquired in step S720, the interpolation image generation unit 610 generates an interpolation image in the interpolation time phase. Then, the interpolation image generation unit 610 outputs the generated interpolation image to the combining position acquisition unit 140 and the combined image generation unit 150 as a time phase image in the second moving image corresponding to a time phase image to which attention is paid in the first moving image.

The interpolation image is generated based on the time-series motion of the subject in time phase images near the interpolation time phase.

For example, a case is considered where an interpolation image in the 4.5th time phase that is an interpolation time phase of the second moving image associated with a time phase image in the fifth time phase of the first moving image is generated. In this case, the interpolation image is generated based on a time-series motion between time phase images in the fourth and fifth time phases, which are time phase images before and after the 4.5th time phase of the second moving image. That is, deformation information between the fourth and fifth time phases is estimated, and for example, the image in either one of the time phases is deformed, to generate the interpolation image. In this operation, the interpolation image representing the state of the subject between the time phase images in the fourth and fifth time phases is generated by interpolating the deformation information. Specifically, in a case where the time phase image in the fifth time phase is deformed, the time phase image in the fifth time phase is deformed using deformation information obtained by multiplying the amount of deformation for deforming the time phase image in the fifth time phase into the time phase image in the fourth time phase by an interpolation rate obtained from the interpolation time phase, whereby the interpolation image is generated. In the above case, for example, 5 (-th time phase)−4.5 (-th time phase)=0.5 is used as the interpolation rate. Consequently, it is possible to generate the interpolation image representing the state of the subject between the fourth and fifth time phases.

Time phases that are used to generate an interpolation image may not be adjacent time phases before and after the interpolation time phase. For example, an interpolation image can also be generated by estimating deformation information between the b-th time phase before the interpolation time phase b+f and the b+d-th time phase after the interpolation time phase b+f and deforming the time phase image in the b+d-th time phase using deformation information obtained by multiplying the amount of deformation by a value of (d−f)/d. Alternatively, a value (an interpolation rate) by which the deformation information is to be multiplied may be obtained based on phase parameters in two time phases between which the deformation information is to be estimated.

Two time phases that are used to estimate deformation information may not be time phases before and after an interpolation time phase. For example, as an example, a case is considered where an interpolation image in the first moving image having a phase similar to that of a time phase image 825 in the seventh time phase of the second moving image illustrated in FIG. 8 is generated. In this case, the interpolation image may be generated by estimating deformation information between the time phase image 810 in the sixth time phase and a time phase image 820 in the seventh time phase of the first moving image and extrapolating the deformation information.

In FIG. 8, a value of the second phase parameter of the time phase image 825 in the seventh time phase of the second moving image is a value between values of the first phase parameter of a time phase image in the second time phase and a time phase image in the third time phase of the first moving image. Thus, it can be estimated that the phase is between these two time phases. Thus, an interpolation image in an interpolation time phase of the first moving image corresponding to the time phase image 825 in the seventh time phase of the second moving image may be generated by estimating deformation information between time phase images in the second and third time phases of the first moving image and deforming the time phase image in either one of the second and third time phases.

As the method for estimating deformation information according to the present exemplary embodiment, a method similar to that in step S250 in the first exemplary embodiment can be used.

Based on the above, the processing of the image processing apparatus 60 is performed.

By the above-described methods, a combined image obtained by combining time phase images similar in a tidal volume in lungs as an observation target can be generated. That is, even in a case where a pace of respiratory movement is different between when the first moving image is captured and when the second moving image is captured, time phase images corresponding to any tidal volume can be combined together. Then, the user observes, in time series, combined images each obtained by combining time phase images similar in a tidal volume and thus can easily observe motion of the entire region of the lungs. Since a degree of slippage can be calculated based on combined images in which phases are associated with each other more appropriately. Therefore, it is possible to calculate a degree of slippage with higher accuracy.

Other Exemplary Embodiments

The technique according to the present invention can employ exemplary embodiments as, for example, a system, an apparatus, a method, a program, and a recording medium (a storage medium). Specifically, the technique according to the present invention may be applied to a system including a plurality of devices (e.g., a host computer, an interface device, an imaging apparatus, and a web application), or may be applied to an apparatus composed of a single device.

The purpose of the technique according to the present invention is achieved as follows. That is, a recording medium (or a storage medium) that records a program code (a computer program) of software for achieving the functions of the above exemplary embodiments is supplied to a system or an apparatus. This storage medium is a computer-readable storage medium. Then, a computer (or a CPU or a microprocessor unit (MPU)) of the system or the apparatus reads and executes the program code stored in the recording medium. In this case, the program code itself read from the recording medium achieves the functions of the above exemplary embodiments, and the recording medium that records the program code constitutes the technique according to the present invention.

The present invention is not limited to the above exemplary embodiments. Various modifications (including the organic combinations of the exemplary embodiments) can be made based on the spirit of the present invention, and are not excluded from the scope of the present invention. That is, all the configurations obtained by combining the above exemplary embodiments and their variations are also included in the exemplary embodiments of the present invention.

The present invention is not limited to the above exemplary embodiments, and can be changed and modified in various manners without departing from the spirit and the scope of the present invention. Thus, the following claims are appended to publicize the scope of the present invention.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present invention, even in a case where a region of a part as an observation target included in an image capturing range is different between a plurality of medical images in different time phases, a degree of slippage of the region of the part as the observation target can be calculated with high accuracy.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a moving image acquisition unit configured to acquire a first moving image and a second moving image that have been obtained by capturing a target object from positions different from each other using an imaging apparatus;
a generation unit configured to generate a first combined image by combining a first reference image obtained from the first moving image and a second reference image obtained from the second moving image, and generate a second combined image by combining a first comparison image obtained from the first moving image and a second comparison image obtained from the second moving image; and
a degree-of-slippage calculation unit configured to calculate a degree of slippage of the target object, based on deformation information estimated from the first combined image and the second combined image.

2. The image processing apparatus according to claim 1, wherein the degree of slippage is a relative amount of movement between two reference points that are set inside the target object and outside the target object across a contour line of the target object, respectively, the relative amount of movement being calculated based on a position on the first combined image and a position on the second combined image of the two reference points.

3. The image processing apparatus according to claim 1, wherein the target object is an organ that makes a periodic movement,
wherein the image processing apparatus further comprises:
a phase acquisition unit configured to acquire a first phase parameter indicating phase information regarding a motion of the target object in time phases of the first moving image, and a second phase parameter indicating phase information regarding a motion of the target object in time phases of the second moving image; and
an association unit configured to associate, based on the first phase parameter and the second phase parameter, a plurality of time phase images including the first reference image and the first comparison image obtained from the first moving image and a plurality of time phase images including the second reference image and the second comparison image obtained from the second moving image, and
wherein the first reference image and the second reference image and the first comparison image and the second comparison image are associated with each other by the association unit.

4. The image processing apparatus according to claim 3, wherein the phase acquisition unit acquires the first phase parameter, based on a state of the target object captured in the first moving image, and acquires the second phase parameter, based on a state of the target object captured in the second moving image.

5. The image processing apparatus according to claim 3, wherein the association unit associates time phase images having the first phase parameter and the second phase parameter that are similar to each other.

6. The image processing apparatus according to claim 3, wherein the association unit associates time phase images inside the target object having the first phase parameter and the second phase parameter similar to each other, and associates time phase images outside the target object having the first phase parameter and the second phase parameter similar to each other.

7. The image processing apparatus according to claim 3, further comprising a calculation unit configured to calculate a reliability of a combining position of a time phase image obtained from the first moving image and a time phase image obtained from the second moving image that are associated with each other by the association unit.

8. The image processing apparatus according to claim 7, wherein the generation unit selects at least two or more pairs of time phase images having the reliability of greater than or equal to a threshold and generates a combined image.

9. The image processing apparatus according to claim 7,
wherein the generation unit generates at least three or more combined images from time phase images obtained from the first moving image and time phase images obtained from the second moving image, and
wherein the degree-of-slippage calculation unit selects two or more combined images having the reliability of greater than or equal to a threshold from among the three or more combined images, and calculates a degree of slippage of the target object, based on deformation information estimated from the selected combined images.

10. The image processing apparatus according to claim 1, wherein the generation unit generates at least one of the first reference image and the first comparison image from at least one time phase image obtained from the first moving image.

11. The image processing apparatus according to claim 1, wherein the generation unit generates at least one of the second reference image and the second comparison image from at least one time phase image obtained from the second moving image.

12. The image processing apparatus according to claim 1,
wherein the generation unit further generates a third combined image by combining the first reference image and a third reference image obtained from the second moving image, and
wherein the degree-of-slippage calculation unit calculates a degree of slippage of the target object, based on first deformation information estimated from the first combined image and the second combined image and second deformation information estimated from the first combined image and the third combined image.

13. The image processing apparatus according to claim 1, wherein the degree-of-slippage calculation unit calculates a degree of slippage of the target object, based on deformation information inside the target object and deformation information outside the target object that are estimated from the first combined image and the second combined image.

14. An image processing apparatus comprising:
a moving image acquisition unit configured to acquire a first moving image and a second moving image that have been obtained by capturing a target object from positions different from each other using an imaging apparatus;
a combining position information acquisition unit configured to acquire combining position information between a first reference image obtained from the first moving image and a second reference image obtained from the second moving image; and
a degree-of-slippage calculation unit configured to calculate a degree of slippage of the target object based on:
the combining position information;
first deformation information estimated from the first reference image and a first comparison image obtained from the first moving image;
second deformation information estimated from the second reference image and a second comparison image obtained from the second moving image; and
third deformation information estimated from at least one of a pair of the first reference image and the second comparison image and a pair of the first comparison image and the second reference image.

15. An image processing apparatus comprising:
a moving image acquisition unit configured to acquire a first moving image and a second moving image that have been obtained by capturing a target object from positions different from each other using an imaging apparatus;
a generation unit configured to generate a combined image obtained by combining a first reference image obtained from the first moving image and a second reference image obtained from the second moving image; and
a degree-of-slippage calculation unit configured to calculate a degree of slippage of the target object, based on first deformation information estimated from the combined image and a first comparison image obtained from the first moving image and second deformation information estimated from the combined image and a second comparison image obtained from the second moving image.

16. The image processing apparatus according to claim 1, wherein the imaging apparatus is an X-ray computed tomography (CT) apparatus, and the first moving image and the second moving image are four-dimensional CT images.

17. The image processing apparatus according to claim 1, wherein the target object is a pair of lungs, and the first moving image and the second moving image are moving images obtained by capturing the lungs in a divided manner in a craniocaudal direction.

18. The image processing apparatus according to claim 3, wherein the association unit associates a time phase image at a maximal inspiratory level obtained from the first moving image and a time phase image at the maximal inspiratory level obtained from the second moving image, and associates a time phase image at a maximal expiratory level obtained from the first moving image and a time phase image at the maximal expiratory level obtained from the second moving image.

19. An image processing method comprising:

acquiring a first moving image and a second moving image that are obtained by capturing a target object from positions different from each other using an imaging apparatus;

generating a first combined image by combining a first reference image obtained from the first moving image and a second reference image obtained from the second moving image, and generating a second combined image by combining a first comparison image obtained from the first moving image and a second comparison image obtained from the second moving image; and calculating a degree of slippage of the target object, based on deformation information estimated from the first combined image and the second combined image.

20. A non-transitory computer-readable storage medium that stores a program for causing a computer to execute the units of the image processing apparatus according to claim 1.

* * * * *